United States Patent [19]

van der Jagt

[11] Patent Number: Plant 6,082

[45] Date of Patent: Jan. 12, 1988

[54] CHRYSANTHEMUM NAMED "READY"

[75] Inventor: Martinus R. H. van der Jagt, Ter-Aar, Netherlands

[73] Assignee: Chrysanthemum Breeders Association NV, Netherlands Antilles

[21] Appl. No.: 782,100

[22] Filed: Sep. 30, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

The present invention is a new and distinct variety of Chrysanthemum having a yellow anemone type bloom.

3 Drawing Figures

BACKGROUND OF THE INVENTION

The present invention comprises a new and distinct cultivar of Chrysanthemum plant which is a cross of unknown parents. The invention was discovered by Martinus van der Jagt in June 1981 at Baradÿsweg 88, Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of Chrysanthemum is shown in the accompanying drawings, the color being as nearly true as possible with color photographs of this type.

FIG. 1 shows the full bloom of the new cultivar.

FIG. 2 shows various stages of bloom of the new cultivar.

FIG. 3 shows the foliage and stem of the new cultivar.

DESCRIPTION OF THE INVENTION

This new variety of Chrysanthemum is of the botanical classification *Chrysanthemum morifolium* named Ready. When grown in the vicinity of Ter Aar, Holland, it has a response time of approximately 9 weeks. This new variety produces medium to large sized blooms having a two weeks performance.

This new variety of Chrysanthemum has been found to retain its distinctive characteristics throughout successive propagations and may be planted under greenhouse conditions in Holland between weeks 5 and 35.

The following is a description of the plant and characteristics that distinguish it over related known varieties and its antecedents.

Bud:

*Size.*—Large.
*Form.*—Round and high.
*Color.*—Primrose yellow, RHS 601/1.

Botanical classification: *Chrysanthemum morifolium.*

Bloom:

*Size.*—Medium to large.
*Fully open.*—8–9 cms.
*Borne.*—Singly.
*Stems.*—Strong.
*Form.*—Anemone type.
*Permanence.*—14 days.

Color:

*Center of flower.*—(Disk) Buttercup yellow RHS 5/2–5.
*Petals.*—Near white at ray petal edges with a central portion ranging from Primrose yellow RHS 601/3 to 601/2 at maturity.
*Tonality from a distance.*—A big yellow anemone type with a large disk.
*Discoloration.*—To a pale yellow.

Petals:

*Texture.*—Smooth (both upper and underside).
*Number.*—Normally 25–28 in two rows.
*Arrangement.*—Mostly next to each other, some imbricated.
*Persistence.*—Petals not so strong, but don't reflex.
*Fragance.*—Chrysanthemum.

Reproductive organs:

*Stamens.*—Few, small.
*Pollen.*—Few, in the disk (cushion).
*Styles.*—Columnar.
*Length.*—Short, thin.
*Stigmas.*—Small yellow.
*Ovaries.*—Enclosed in calyx.

Plant:

*Form.*—Herbaceous.
*Growth.*—Vigorous.
*Height.*—Medium.
*Peduncle.*—Strong.

Foliage:

*Color.*—Normal to dark.
*Size.*—Medium.
*Quantity.*—Normal.
*Shape.*—Pointed-oval.
*Texture.*—Fleshy.
*Ribs and veins.*—Ordinary.
*Edge.*—Less undulated.
*Leaf underside.*—Smooth.
*Leaf upperside.*—Rough.

In the description above color references are made to the Horticultural Color Chart I & II issued by the British Colour Council in collaboration with The Royal Horticultural Society, Copyright Robert F. Wilson, Vol I, 1938; Vol II, 1941, printed by Henry Stone & Son LTD, Banbury, England.

I claim:

1. A new and distinctive variety of Chrysanthemum named Ready as described and illustrated in the foregoing specification and accompanying drawings.

* * * * *

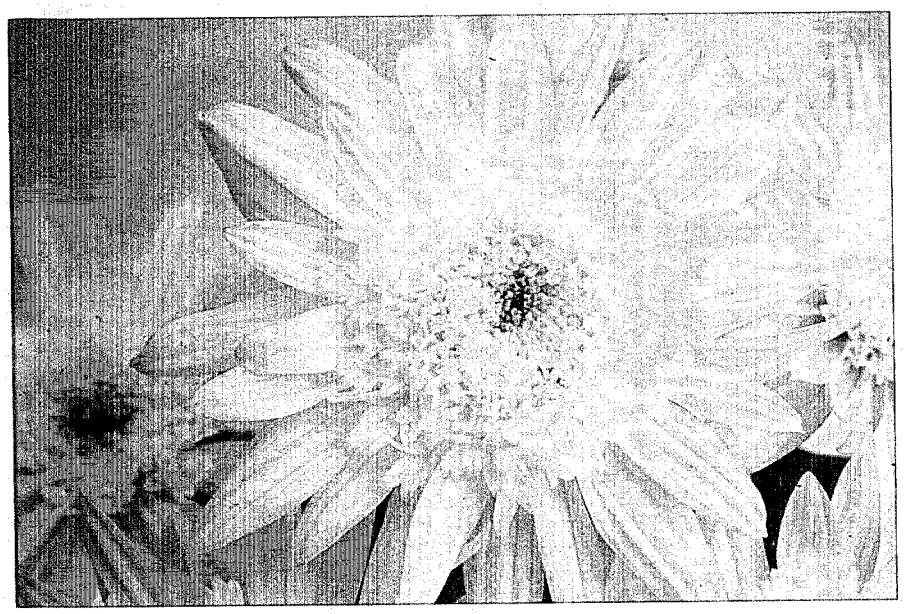

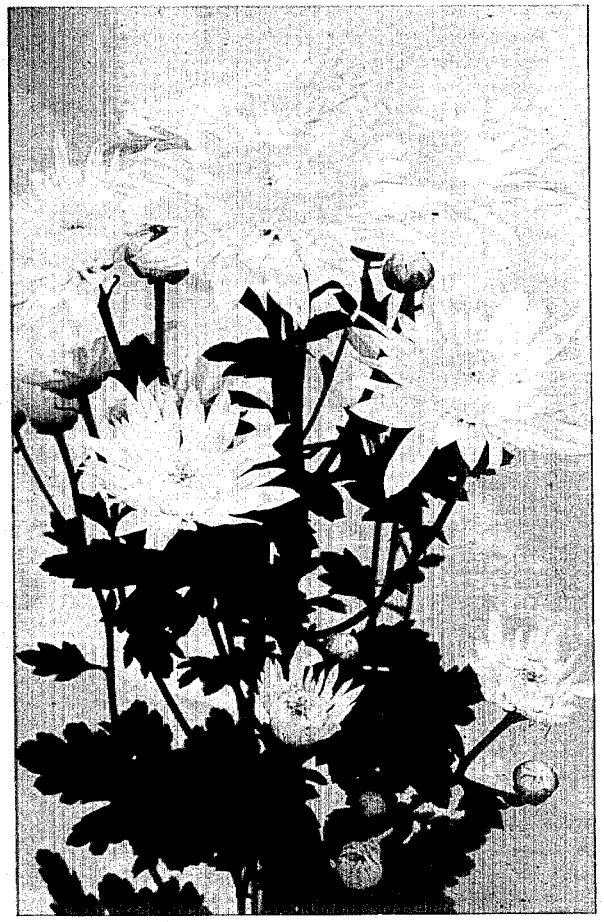

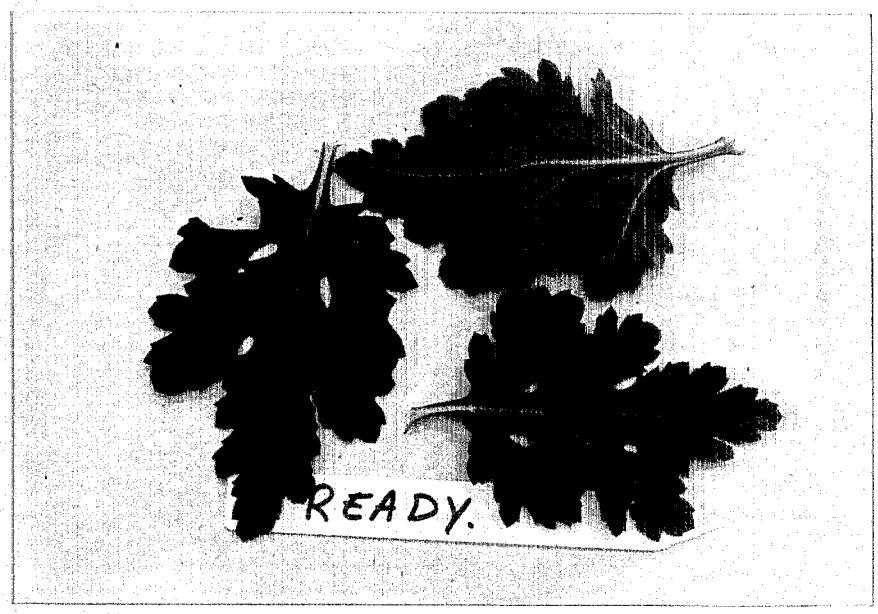
READY.